(12) United States Patent
Wang et al.

(10) Patent No.: US 10,932,923 B2
(45) Date of Patent: Mar. 2, 2021

(54) ANKLE PROSTHESIS HYDRAULIC DRIVE CIRCUIT FOR ACHIEVING DAMPING CONTROL AND ENERGY RECOVERY

(71) Applicant: Beihang University, Beijing (CN)

(72) Inventors: Xingjian Wang, Beijing (CN); Shaoping Wang, Beijing (CN); Rufei Li, Beijing (CN); Jing Fang, Beijing (CN); Changhong Lin, Beijing (CN)

(73) Assignee: Beihang University, Beijing (CN)

( * ) Notice: Subject to any disclaimer, the term of this patent is extended or adjusted under 35 U.S.C. 154(b) by 15 days.

(21) Appl. No.: 16/561,398

(22) Filed: Sep. 5, 2019

(65) Prior Publication Data

US 2020/0229949 A1 Jul. 23, 2020

(30) Foreign Application Priority Data

Jan. 21, 2019 (CN) .......................... 201910053395.4

(51) Int. Cl.
*A61F 2/68* (2006.01)
*A61F 2/66* (2006.01)
*A61F 2/74* (2006.01)
*A61F 2/50* (2006.01)

(52) U.S. Cl.
CPC .............. *A61F 2/68* (2013.01); *A61F 2/6607* (2013.01); *A61F 2002/5006* (2013.01); *A61F 2002/741* (2013.01); *A61F 2002/745* (2013.01); *A61F 2002/748* (2013.01)

(58) Field of Classification Search
CPC .. A61F 2/68; A61F 2/6607; A61F 2002/5006; A61F 2002/741; A61F 2002/745; A61F 2002/748

See application file for complete search history.

(56) References Cited

U.S. PATENT DOCUMENTS

| 2007/0198098 | A1* | 8/2007 | Roston ....................... A61F 2/68 623/26 |
| 2008/0300692 | A1* | 12/2008 | Moser ........................ A61F 2/70 623/55 |
| 2015/0066153 | A1* | 3/2015 | Palmer, III ................. A61F 2/70 623/24 |
| 2015/0134081 | A1* | 5/2015 | Geiger .................. A61F 2/6607 623/47 |
| 2019/0298550 | A1* | 10/2019 | Rumpler ................. A61F 2/604 |

* cited by examiner

*Primary Examiner* — Suba Ganesan
*Assistant Examiner* — Aren Patel
(74) *Attorney, Agent, or Firm* — Troutman Pepper Hamilton Sanders LLP; Christopher C. Close, Jr.

(57) ABSTRACT

The disclosure discloses an ankle prosthesis hydraulic drive circuit for achieving damping control and energy recovery, belonging to the technical field of prosthesiss and orthotic devices. The hydraulic drive circuit particularly includes a motor, a hydraulic pump, a first check valve, a first high-pressure energy accumulator, a three-position four-way valve, an electromagnetic normally-closed valve, a second high-pressure energy accumulator, a single-rod hydraulic cylinder, an electromagnetic normally-opened valve, a low-pressure energy accumulator, a second check valve, an oil inlet line, an oil outlet line, a first line and a second line. The hydraulic drive circuit provided by the disclosure is capable of outputting enough peak power to meet a normal walking demand, and meanwhile actively controlling the damping of the circuit and recycling energy during the walking.

6 Claims, 2 Drawing Sheets

ANKLE PROSTHESIS HYDRAULIC DRIVE CIRCUIT FOR ACHIEVING DAMPING CONTROL AND ENERGY RECOVERY

This application claims priority to Chinese application number 201910053395.4, filed Jan. 21, 2019, with a title of ANKLE PROSTHESIS HYDRAULIC DRIVE CIRCUIT FOR ACHIEVING DAMPING CONTROL AND ENERGY RECOVERY. The above-mentioned patent application is incorporated herein by reference in its entirety.

TECHNICAL FIELD

The disclosure relates to the technical field of prosthesiss and orthotic devices, and relates to an ankle prosthesis hydraulic drive circuit for achieving damping control and energy recovery.

BACKGROUND

Nowadays, the number of people with amputated limbs below knees is increasing gradually due to traffic accidents, diseases and other reasons. For people with amputated lower limbs, the most common manners for compensating their walking capability defects are wheelchairs, walking sticks and prosthesiss. The wheelchair is large in occupied area, and is limited by a wheel type machine so as not to arrive at a place, such as walking by stairs. The use of walking sticks occupies functions of double hands, and reduces the body function of wearing persons. Wearing prosthesiss can achieve the compensation for deficient functions of a human body, and has advantages in the aspects of decoration, walking comfort and the like.

At present, there are a great variety of ankle prostheses, which are mainly classified into passive and active ankle prostheses according to the presence of an active drive force. For the passive ankle prosthesis, rubber, carbon fiber or other materials are adopted to make foot plates, or energy accumulation devices such as a spring is introduced into a mechanism so that the foot entirely has a certain elasticity. The passive ankle prosthesis has the advantages of simple mechanism, light weight, low energy consumption and the like, but the passive ankle prosthesis has no power source and has a problem that the walking of the amputated patient is not matched with a movement trail of normal limbs. For the active ankle prosthesis, active drive devices such as a motor is introduced into the prosthesis mechanism. The active ankle prosthesis has the main advantages that the wearing person is natural in tread and can adapt to different road conditions, but the active ankle prosthesis has the defects of large prosthesis system weight, high energy consumption and the like due to introduction of a drive unit. The active ankle prosthesis is divided into a motor drive ankle prosthesis and a hydraulic drive ankle prosthesis based on different drive elements. The present ankle prosthesis commonly adopts a motor drive mode, but the motor drive ankle prosthesis has the defects of slow response speed and insufficient output torque. Although the hydraulic drive active ankle prosthesis has the advantages that torque is large and damping and buffer can be provided, due to low energy efficiency, it is too large in mass and endurance is difficult to ensure. Furthermore, the present hydraulic ankle prosthesis also has a problem of poor adaptation caused by a fact that damping cannot be timely adjusted.

SUMMARY

In order to solve the prosthesis endurance and adaption problems existing in the prior art, the disclosure aims to provide an ankle prosthesis hydraulic drive circuit for achieving damping control and energy recovery, which is capable of outputting enough peak power to meet a normal walking demand, and meanwhile actively controlling the damping of the circuit and recycling energy during the walking.

Provided is an ankle prosthesis hydraulic drive circuit for achieving damping control and energy recovery, the hydraulic drive circuit including a motor, a hydraulic pump, a first check valve, a first high-pressure energy accumulator, a three-position four-way valve, an electromagnetic normally-closed valve, a second high-pressure energy accumulator, a single-rod hydraulic cylinder, an electromagnetic normally-opened valve, a low-pressure energy accumulator, a second check valve, an oil inlet line, an oil outlet line, a first line and a second line.

The three-position four-way valve has a P port, an O port, an A port and a B port; when the three-position four-way valve is at a left position, the P port is connected with the A port, and the O port is connected with the B port; when the three-position four-way valve is at a middle position, the P port is cut off, and the O port is connected with the A port and the B port; when the three-position four-way valve is at a right position, the P port is connected with the B port, and the O port is connected with the A port.

The motor continuously drives the hydraulic pump to work; in the hydraulic drive circuit, the oil outlet of the hydraulic pump is connected with the P port of the three-position four-way valve through the oil inlet line, the A port of the three-position four-way valve is connected with the upper cavity of the single-rod hydraulic cylinder through the second line, the oil inlet of the hydraulic pump is connected with the O port of the three-position four-way valve through the oil outlet line, the B port of the three-position four-way valve is connected with the lower cavity of the single-rod hydraulic cylinder through the first line, the first check valve and the first high-pressure energy accumulator are connected to the oil inlet line, the first check valve is located between the oil outlet of the hydraulic pump and the first high-pressure energy accumulator, the second check valve and the low-pressure energy accumulator are connected to the oil outlet line, the second check valve is located between the oil inlet of the hydraulic pump and the low-pressure energy accumulator, the electromagnetic normally-opened valve is connected to the first line, the electromagnetic normally-closed valve and the second high-pressure energy accumulator are connected to the second line, and the second high-pressure energy accumulator is located between the electromagnetic normally-closed valve and the single-rod hydraulic cylinder.

The disclosure has the advantages and active effects:

(1) In the disclosure, the real-time control of the damping of the prosthesis is achieved through the high-speed on-off of the check valve, a more smooth walking effect is achieved by means of a tiny mechanism, and meanwhile the artificial lamb can adapt to a more complex road surface.

(2) In the disclosure, the second high-pressure energy accumulator recovers energy from the dropping of the prosthesis when doing negative power in a passive state, and releases the accumulated energy in an active state, thereby achieving the recycling of energy and reducing the energy consumption of a whole period to a great extent so as to improve endurance capability.

(3) In the disclosure, the first high-pressure energy accumulator continuously charges energy through the pump source in a passive state, and is connected with the second high-pressure energy accumulator in an active state to jointly release energy so as to meet the demand of the ankle prosthesis on huge output power and meanwhile reduce the demand on pump source power.

(4) In the disclosure, the single-rod hydraulic cylinder charges oil through a rod-free cavity when in a plantar flexion state, and charges oil through a rod cavity when in a dorsal flexure state so as to achieve a larger output force in the plantar flexion state and achieve faster action in the dorsal flexure state, which is matched with characteristics of a biological ankle and reduces demand amounts of various action states on high-pressure oil.

In drawings, 1, motor; 2, hydraulic pump; 3, first check valve; 4, first high-pressure energy accumulator; 5, first pressure sensor; 6, three-position four-way valve; 7, electromagnetic normally-closed valve; 8, second high-pressure energy accumulator; 9, second pressure sensor; 10, single-rod hydraulic cylinder; 11, prosthesis foot plate; 12, third pressure sensor; 13, electromagnetic normally-opened valve; 14, low-pressure energy accumulator; 15, second check valve; 16, oil inlet line; 17, oil outlet line; 18, first line; 19, second line.

DESCRIPTION OF THE EMBODIMENTS

Next, the disclosure will be further described in detail in combination with drawings and examples.

Figure 1:
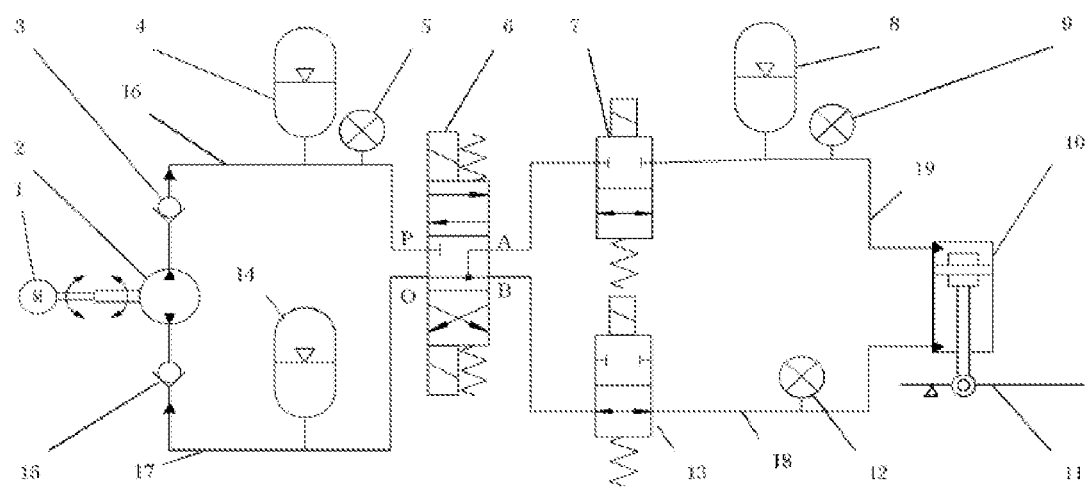
FIG. 1 is a diagram of a hydraulic circuit state at an HS stage according to the disclosure.

The disclosure provides an ankle prosthesis hydraulic drive circuit for achieving damping control and energy recovery. As shown in FIG. 1, the hydraulic drive circuit particularly includes a motor 1, a hydraulic pump 2, a first check valve 3, a first high-pressure energy accumulator 4, a three-position four-way valve 6, an electromagnetic normally-closed valve 7, a second high-pressure energy accumulator 8, a single-rod hydraulic cylinder 10, an electromagnetic normally-opened valve 13, a low-pressure energy accumulator 14, a second check valve 15, an oil inlet line 16, an oil outlet line 17, a first line 18 and a second line 19; the middle of the single-rod hydraulic cylinder 10 is provided with a piston, an upper cavity is above the piston, a lower cavity is under the piston, the piston is fixedly connected with a single rod, and the single rod vertically extends from the lower end surface of the single-rod hydraulic cylinder 10.

The three-position four-way valve 6 has a P port, an O port, an A port and a B port; when the three-position four-way valve 6 is at a left position, the P port is connected with the A port, and the O port is connected with the B port; when the three-position four-way valve 6 is at a middle position, the P port is cut off, and the O port is connected with the A port and the B port; when the three-position four-way valve 6 is at a right position, the P port is connected with the B port, and the O port is connected with the A port.

The motor 1 (brushless direct current motor 60BLF993000) continuously drives the hydraulic pump 2 (HYC-MP1F1B/A) to work; in the hydraulic drive circuit, the oil outlet of the hydraulic pump 2 is connected with the P port of the three-position four-way valve 6 through the oil inlet line 16, the A port of the three-position four-way valve is connected with the upper cavity of the single-rod hydraulic cylinder 10 through the second line 19; the oil inlet of the hydraulic pump 2 is connected with the O port of the three-position four-way valve 6 through the oil outlet line 17, the B port of the three-position four-way valve is connected with the lower cavity of the single-rod hydraulic cylinder 10 through the first line 18. The first check valve 3 and the first high-pressure energy accumulator 4 are connected to the oil inlet line 16, the first check valve 3 is located between the oil outlet of the hydraulic pump 2 and the first high-pressure energy accumulator 4, the second check valve 15 and the low-pressure energy accumulator 14 are connected to the oil outlet line 17, the second check valve 15 is located between the oil inlet of the hydraulic pump 2 and the low-pressure energy accumulator 14, the electromagnetic normally-opened valve 13 is connected to the first line 18, the electromagnetic normally-closed valve 7 and the second high-pressure energy accumulator 8 are connected to the second line 19, and the second high-pressure energy accumulator 8 is located between the electromagnetic normally-closed valve 7 and the single-rod hydraulic cylinder 10.

A first pressure sensor 5 is connected to the oil inlet line 16, a second pressure sensor 9 is connected to the second line 19, a third pressure sensor 12 is connected to the first line 18, and the single rod of the single-rod hydraulic cylinder 10 is connected with an prosthesis foot plate 11 through a hinge.

The first check valve 3 is used for preventing the oil in the first high-pressure energy accumulator 4 from flowing back to the hydraulic pump 2; the second check valve 15 is used for preventing the oil in the hydraulic pump 2 from flowing back to the low-pressure energy accumulator 14.

The first pressure sensor 5 is used for detecting the pressure in the first high-pressure energy accumulator 4; the second pressure sensor 9 is used for detecting the pressure in the upper cavity of the single-rod hydraulic cylinder 10; the third pressure sensor 12 is used for detecting the pressure in the lower cavity of the single-rod hydraulic cylinder 10.

The first high-pressure energy accumulator 4 is used for storing oil in the oil inlet line 16; the second high-pressure energy accumulator 8 is used for storing oil in the second line 19; the low-pressure energy accumulator 14 is used for storing oil in the oil outlet line 17.

By controlling the three-position four-way valve 6, the hydraulic drive circuit is switched among an active plantar flexion state, a passive state and an active dorsal flexure state. Switching between a passive plantar flexion state and a passive dorsal flexure state is achieved through the electromagnetic normally-closed valve 7. When the hydraulic drive circuit is in a passive state and the electromagnetic normally-closed valve 7 is conductive, the hydraulic drive circuit is in the passive plantar flexion state; when the hydraulic drive circuit is in the passive state and the electromagnetic normally-closed valve 7 is turned off, the hydraulic drive circuit is in the passive dorsal flexure state. Through matching of the three-position four-way valve 6 and the electromagnetic normally-closed valve 7, the prosthesis composed of the hydraulic drive circuit and the artificial lamb foot plate 11 has four states corresponding to a human body walking period.

Damping control is achieved through high-speed on-off of the electromagnetic normally-opened valve 13. When the prosthesis is in the passive state, the high-speed on-off of the electromagnetic normally-opened valve 13 is achieved by applying drive current of a PWM wave form to the electromagnetic normally-opened valve 13 so that the electromagnetic normally-opened valve may provide damping. Real-time control of the damping of the electromagnetic normally-opened valve 13 can be achieved by adjusting the duty ratio of the drive current of a PWM wave form in real time, thereby achieving real-time control of the artificial lamb damping. Energy recovery is achieved through the second high-pressure energy accumulator 8.

EXAMPLE

The three-position four-way valve 6 is matched with the electromagnetic normally-closed valve 7 so that the artificial lamb has four states corresponding to a human body walking period as follows:

(1) A state 1 corresponds to the HS (Heel Strike) process of a people walking period. As shown in FIG. 1, at this moment, the three-position four-way valve 6 is in the middle position, the electromagnetic normally-closed valve 7 is in a conductive state, and the electromagnetic normally-opened valve 13 is in the conductive state. At this moment, the hydraulic force of the low-pressure energy accumulator 14 and human body gravity jointly drive a piston in the single-rod hydraulic cylinder 10 to downwardly move, the ankle prosthesis located on the artificial foot plate 11 undergoes plantar flexion movement, and meanwhile the resistance of the joint is controlled through the high-speed on-off of the electromagnetic normally-opened valve 13, and meanwhile the hydraulic pump 2 continuously charges oil to the first high-pressure energy accumulator 4.

Figure 2:
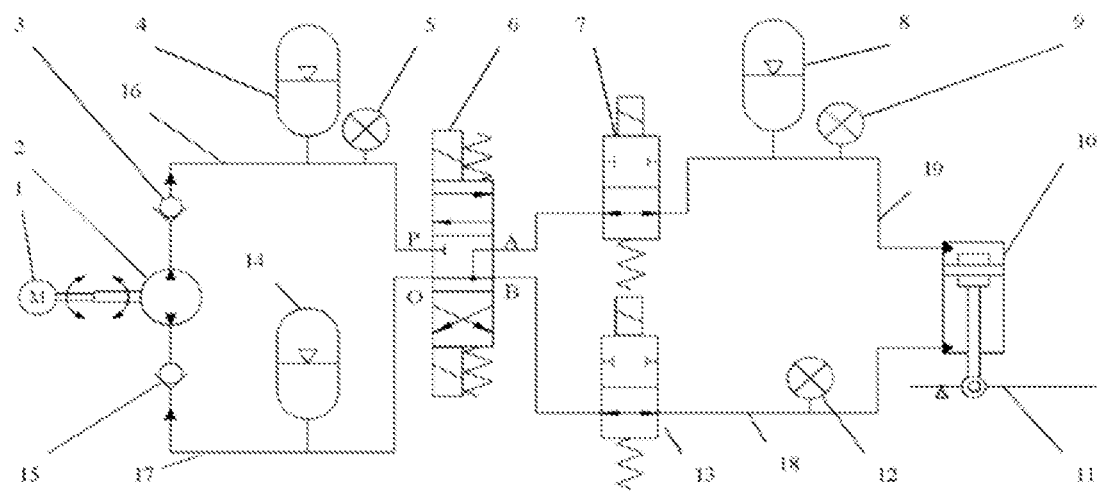
FIG. 2 is a diagram of a hydraulic circuit state at an MS stage according to the disclosure.

(2) A state 2 corresponds to the MS (Middle Stance) process of a people walking period. As shown in FIG. 2, at this moment, the three-position four-way valve 6 is at the middle position, the electromagnetic normally-closed valve 7 is in a turn-off state, and the electromagnetic normally-opened valve 13 is in a conductive state. At this moment, the upper cavity of the single-rod hydraulic cylinder 10 is connected with the second high-pressure energy accumulator 8 through the second line 19, the lower cavity of the single-rod hydraulic cylinder 10 is connected with the low-pressure energy accumulator 14 through the first line 18 and the oil outlet line 17. Since a human body moves forward at this moment, the ankle undergoes passive dorsal flexure, during this process, the piston in the single-rod hydraulic cylinder 10 upwardly moves to extrude oil into the second high-pressure energy accumulator 8, and meanwhile the electromagnetic normally-opened valve 13 controls an ankle to output the resistance through high-speed on-off, and during this process, the hydraulic pump 2 continuously charges oil to the first high-pressure energy accumulator 4.

Figure 3:
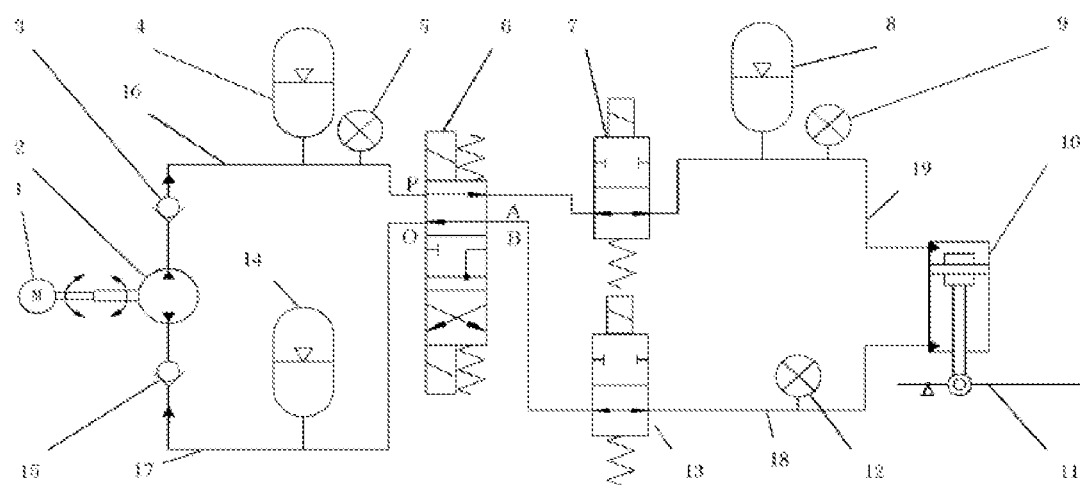
FIG. 3 is a diagram of a hydraulic circuit state at a TS stage according to the disclosure.

(3) A state 3 corresponds to the TS (Terminal Stance) process of a people walking period. As shown in FIG. 3, when dorsal flexure is performed to a maximal angle, active kicking state is performed, at this moment, the three-position four-way valve 6 is at the left position, the electromagnetic normally-closed valve 7 is in the conductive state, and the electromagnetic normally-opened valve 13 is in the conductive state. At this moment, the upper cavity of the single-rod hydraulic cylinder 10 is connected with the second high-pressure energy accumulator 8 through the second line 19 and simultaneously connected with the first high-pressure energy accumulator 4 through the oil inlet line 16, and the lower cavity of the single-rod hydraulic cylinder 10 is connected with the low-pressure energy accumulator 14 through the first line 18 and the oil outlet line 17. Oil accumulated by the second high-pressure energy accumulator 8 and oil accumulated by the first high-pressure energy accumulator 4 are jointly discharged at this moment to provide enough power and moment of force for pushing a human body to advance.

Figure 4:
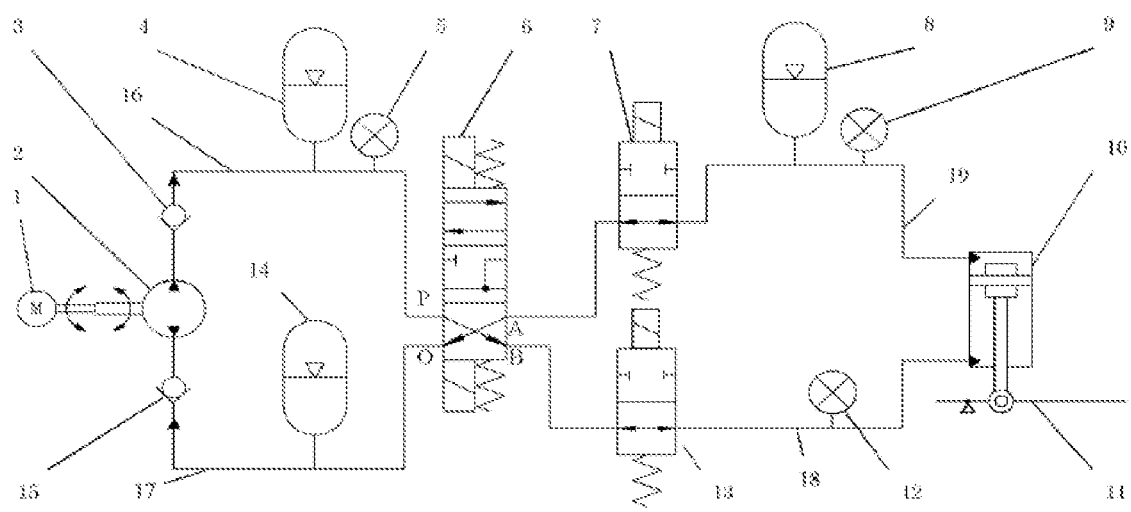
FIG. 4 is a diagram of a hydraulic circuit state at a WS stage according to the disclosure.

(4) A state 4 corresponds to the SW (Swing) process of a people walking period. As shown in FIG. 4, at this moment, the three-position four-way valve 6 is at the right position, the electromagnetic normally-closed valve 7 is in the conductive state, and the electromagnetic normally-opened valve 13 is in the conductive state. At this moment, the lower cavity of the single-rod hydraulic cylinder 10 is connected with the first high-pressure energy accumulator 4 through the first line 18 and the oil outlet line 16, and the upper cavity of the single-rod hydraulic cylinder 10 is connected with the second high-pressure energy accumulator 8 through the second line 19 and simultaneously connected with the low-pressure energy accumulator 14 through the oil outlet line 17, and at this moment, the hydraulic pump 2 directly drives the piston of the single-rod hydraulic cylinder 10 to fast upwardly move so that the state of the prosthesis is restored.

What is claimed is:

1. An ankle prosthesis hydraulic drive circuit for achieving damping control and energy recovery, the hydraulic drive circuit comprising a motor, a hydraulic pump, a first check valve, a first high-pressure energy accumulator, a three-position four-way valve, an electromagnetic normally-closed valve, a second high-pressure energy accumulator, a single-rod hydraulic cylinder, an electromagnetic normally-opened valve, a low-pressure energy accumulator, a second check valve, an oil inlet line, an oil outlet line, a first line and a second line;

wherein, the three-position four-way valve has a P port, an O port, an A port and a B port; when the three-position four-way valve is at a left position, the P port is connected with the A port, and the O port is connected with the B port; when the three-position four-way valve is at a middle position, the P port is cut off, and the O port is connected with the A port and the B port; when the three-position four-way valve is at a right position, the P port is connected with the B port, and the O port is connected with the A port;

the motor continuously drives the hydraulic pump to work; in the hydraulic drive circuit, the oil outlet of the hydraulic pump is connected with the P port of the three-position four-way valve through the oil inlet line, the A port of the three-position four-way valve is connected with the upper cavity of the single-rod hydraulic cylinder through the second line, the oil inlet of the hydraulic pump is connected with the O port of the three-position four-way valve through the oil outlet line, the B port of the three-position four-way valve is connected with the lower cavity of the single-rod hydraulic cylinder through the first line, the first check valve and the first high-pressure energy accumulator are connected to the oil inlet line, the first check valve is located between the oil outlet of the hydraulic pump and the first high-pressure energy accumulator, the second check valve and the low-pressure energy accumulator are connected to the oil outlet line, the second check valve is located between the oil inlet of the hydraulic pump and the low-pressure energy accumulator, the electromagnetic normally-opened valve is connected to the first line, the electromagnetic normally-closed valve and the second high-pressure energy accumulator are connected to the second line, and the second high-pressure energy accumulator is located between the electromagnetic normally-closed valve and the single-rod hydraulic cylinder.

2. The ankle prosthesis hydraulic drive circuit for achieving damping control and energy recovery according to claim 1, wherein, a first pressure sensor is connected to the oil inlet line, a second pressure sensor is connected to the second line, a third pressure sensor is connected to the first line, and the single rod of the single-rod hydraulic cylinder is connected with an prosthesis foot plate through a hinge.

3. The ankle prosthesis hydraulic drive circuit for achieving damping control and energy recovery according to claim 1, wherein, corresponding to the HS process of a people walking period, the three-position four-way valve is at the middle position, the electromagnetic normally-closed valve is in a conductive state, and the electromagnetic normally-opened valve is in the conductive state; the hydraulic force of the low-pressure energy accumulator and human body gravity jointly drive a piston in the single-rod hydraulic cylinder to downwardly move, the resistance of the joint is controlled through the high-speed on-off of the electromagnetic normally-opened valve, and meanwhile the hydraulic pump continuously charges oil to the first high-pressure energy accumulator.

4. The ankle prosthesis hydraulic drive circuit for achieving damping control and energy recovery according to claim 1, wherein, corresponding to the MS process of a people walking period, the three-position four-way valve is at the middle position, the electromagnetic normally-closed valve is in a closed state, and the electromagnetic normally-opened valve is in a conductive state; the upper cavity of the single-rod hydraulic cylinder is connected with the second high-pressure energy accumulator through the second line, the lower cavity of the single-rod hydraulic cylinder is connected with the low-pressure energy accumulator through the first line and the oil outlet line, during this process, the piston in the single-rod hydraulic cylinder upwardly moves to extrude oil into the second high-pressure energy accumulator, and meanwhile the electromagnetic normally-opened valve controls an ankle to output the resistance by means of high-speed on-off, and during this process, the hydraulic pump continuously charges oil to the first high-pressure energy accumulator.

5. The ankle prosthesis hydraulic drive circuit for achieving damping control and energy recovery according to claim 1, wherein, corresponding to the TS process of a people walking period, the three-position four-way valve is at the left position, the electromagnetic normally-closed valve is in the conductive state, and the electromagnetic normally-opened valve is in the conductive state; the upper cavity of the single-rod hydraulic cylinder is connected with the second high-pressure energy accumulator through the second line and simultaneously connected with the first high-pressure energy accumulator through the oil inlet line, and the lower cavity of the single-rod hydraulic cylinder is connected with the low-pressure energy accumulator through the first line and the oil outlet line; oil accumulated by the second high-pressure energy accumulator and oil accumulated by the first high-pressure energy accumulator are jointly discharged at this moment.

6. The ankle prosthesis hydraulic drive circuit for achieving damping control and energy recovery according to claim 1, wherein, corresponding to the SW process of a people walking period, the three-position four-way valve is at the right position, the electromagnetic normally-closed valve is in the conductive state, and the electromagnetic normally-opened valve is in the conductive state; the lower cavity of the single-rod hydraulic cylinder is connected with the first high-pressure energy accumulator through the first line and the oil outlet line, and the upper cavity of the single-rod hydraulic cylinder is connected with the second high-pressure energy accumulator through the second line and simultaneously connected with the low-pressure energy accumulator through the oil inlet line, and the hydraulic pump directly drives the piston of the single-rod hydraulic cylinder to upwardly move.

* * * * *